United States Patent
Petersen et al.

(10) Patent No.: US 11,303,270 B2
(45) Date of Patent: Apr. 12, 2022

(54) PULSE CANCELLATION COMPENSATION METHOD FOR CONTRAST AGENT IMAGING

(71) Applicant: Siemens Medical Solutions USA, Inc., Malvern, PA (US)

(72) Inventors: David A. Petersen, Fall City, WA (US); HanSang Ji, Yongin-si (KR); MinHo Ryu, Yongin-si (KR)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1157 days.

(21) Appl. No.: 15/821,215

(22) Filed: Nov. 22, 2017

(65) Prior Publication Data

US 2018/0367126 A1     Dec. 20, 2018

(51) Int. Cl.
| | |
|---|---|
| *H03K 5/08* | (2006.01) |
| *G01S 7/52* | (2006.01) |
| *A61B 8/00* | (2006.01) |
| *A61B 8/14* | (2006.01) |
| *A61B 8/08* | (2006.01) |

(52) U.S. Cl.
CPC .............. *H03K 5/08* (2013.01); *A61B 8/14* (2013.01); *A61B 8/481* (2013.01); *A61B 8/54* (2013.01); *G01S 7/5202* (2013.01); *G01S 7/52046* (2013.01); *A61B 8/488* (2013.01); *A61B 8/5269* (2013.01)

(58) Field of Classification Search
CPC .. H03K 5/08; A61B 8/14; A61B 8/481; A61B 8/54; A61B 8/488; A61B 8/5269; G01S 7/5202; G01S 7/52046
See application file for complete search history.

(56) References Cited

U.S. PATENT DOCUMENTS

| | | | |
|---|---|---|---|
| 5,632,277 A | 5/1997 | Chapman et al. | |
| 6,155,981 A | 12/2000 | Ermert et al. | |

(Continued)

FOREIGN PATENT DOCUMENTS

| | | | |
|---|---|---|---|
| CN | 1043201 A | 6/1990 | |
| CN | 1162250 A | 10/1997 | |

(Continued)

*Primary Examiner* — Catherine B Kuhlman
*Assistant Examiner* — Sean A Frith

(57) ABSTRACT

A method and an ultrasound system are provided for generating transmission signals of an ultrasound probe used in a contrast-enhanced ultrasound image mode. The ultrasound system generates a pair of pulse control signals n and n+1 and a damping compensation pulse control signal, generates a pair of pulses n and n+1 having polarities opposite to each other and a damping compensation pulse having a polarity opposite to that of the n+1-th pulse based on the pair of pulse control signals and the damping compensation pulse control signal, transmits transmission signals including the pair of pulses and the damping compensation pulse, generates an ultrasound signal based on the transmission signals, transmits the ultrasound signal to a target object, and acquires echo signals for forming a contrast-enhanced ultrasound image of the target object. The damping compensation pulse is successively generated after generating the pair of pulses.

16 Claims, 6 Drawing Sheets

(56) References Cited

U.S. PATENT DOCUMENTS

| | | | |
|---|---|---|---|
| 6,186,950 B1 * | 2/2001 | Averkiou | A61B 8/06 600/440 |
| 6,193,662 B1 | 2/2001 | Hwang | |
| 7,713,209 B2 | 5/2010 | Guracar | |
| 8,043,219 B2 | 10/2011 | Chomas | |
| 2001/0034485 A1 | 10/2001 | Kawagishi et al. | |
| 2004/0254459 A1 * | 12/2004 | Kristoffersen | B06B 1/0215 600/437 |
| 2005/0241396 A1 * | 11/2005 | Huebler | G01N 29/348 73/597 |
| 2012/0310091 A1 * | 12/2012 | Ohnuma | A61B 8/54 600/443 |
| 2013/0123632 A1 * | 5/2013 | Kaji | A61B 8/4483 600/443 |
| 2014/0221841 A1 * | 8/2014 | Okuda | B06B 1/0677 600/459 |
| 2015/0018677 A1 * | 1/2015 | Yoshiara | A61B 8/481 600/431 |
| 2016/0120515 A1 * | 5/2016 | Arai | G01S 15/8925 600/443 |
| 2017/0276775 A1 * | 9/2017 | Tanter | G01S 15/8959 |

FOREIGN PATENT DOCUMENTS

| | | |
|---|---|---|
| CN | 1416782 A | 5/2003 |
| CN | 101128154 A | 2/2008 |
| CN | 103261909 A | 8/2013 |
| EP | 1293802 A2 | 3/2003 |
| JP | H07231247 A | 8/1995 |
| JP | 2007236820 A | 9/2007 |
| KR | 1020090077102 | 7/2009 |
| KR | 101334375 | 11/2013 |
| KR | 1020170033222 | 3/2017 |
| KR | 1020170042936 | 4/2017 |

* cited by examiner

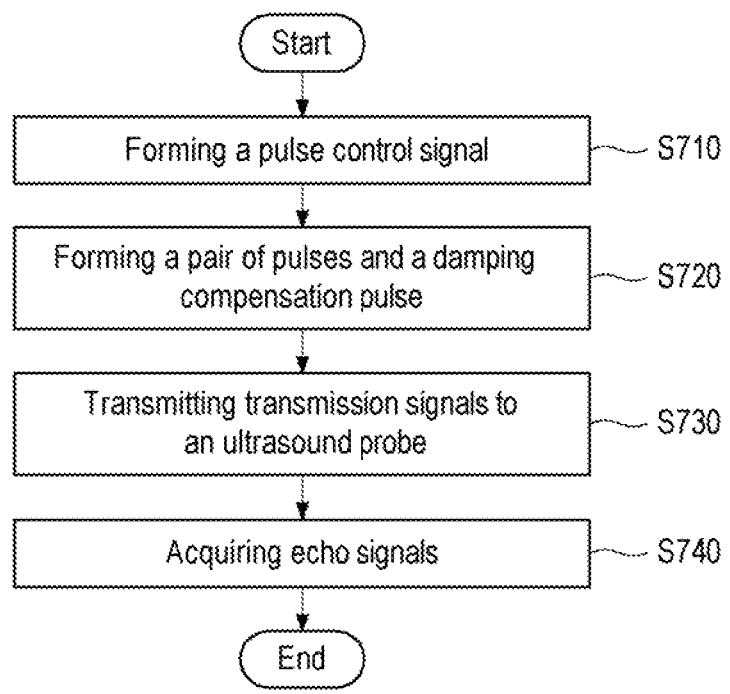

PULSE CANCELLATION COMPENSATION METHOD FOR CONTRAST AGENT IMAGING

TECHNICAL FIELD

The present disclosure relates to a method and an ultrasound system for generating ultrasound signals of an ultrasound probe used in a contrast-enhanced ultrasound image mode.

BACKGROUND

An ultrasound system has been widely used in medical fields to obtain information in a target object due to its non-invasive and non-destructive character. The ultrasound system can provide doctors with high-resolution images of the target object in real time without having to go through an invasive surgical operation on the target object. Therefore, the ultrasound system is used very significantly in the medical fields.

The ultrasound system transmits ultrasound signals to the target object, receives ultrasound echo signals reflected from the target object, and generates ultrasound data by performing signal processing on the received ultrasound echo signals. Further, the ultrasound system generates an ultrasound image by performing a scan conversion or rendering processing on the ultrasound data.

A contrast agent may further be used to clearly observe ultrasound images in a region of interest (ROI) of the target object. In this case, the contrast-enhanced ultrasound images are obtained by using the ultrasound system after the contrast agent is injected into the target object.

In the contrast-enhanced ultrasound mode, a contrast-enhanced ultrasound image of a target object is typically obtained by using a transmitted pulse of a low voltage (about 1 to 5V). If an ultrasound probe generates transmitted pulses of a low voltage, undamped components may be generated due to a capacitive loading effect. In this case, the quality of the contrast-enhanced ultrasound image may be deteriorated as the undamped components may function as noises in the contrast-enhanced ultrasound image.

In a preferred embodiment, contrast-enhanced ultrasound imaging requires a non-inverting pulse and an inverting pulse having polarities opposite to each other to achieve good image quality. The undamped components from the non-inverting and inverting pulses are asymmetric, and could affect pulse cancellation between the non-inverting and inverting pulses. Properly chosen compensation pulses improve the cancellation between the non-inverting and inverting pulses without substantially altering desired transducer response.

SUMMARY

According to one embodiment, a method of generating an ultrasound signal of an ultrasound probe used in a contrast-enhanced ultrasound image mode includes generating a pair of pulse control signals (n, n+1) and a damping compensation pulse control signal; generating a pair of pulses (n, n+1) having polarities opposite to each other and a damping compensation pulse having a polarity opposite to that of the n+1-th pulse based on the pair of pulse control signals and the damping compensation pulse control signal; transmitting transmission signals including the pair of pulses and the damping compensation pulse to the ultrasound probe; and generating an ultrasound signal in the ultrasound probe based on the transmission signals and transmitting the ultrasound signal to a target object, and acquiring echo signals for forming a contrast-enhanced ultrasound image of the target object, wherein the damping compensation pulse is successively generated after generating the pair of pulses.

In the method of generating an ultrasound signal according to the embodiment of the present disclosure, a pulse width of the damping compensation pulse has a value lower than a reciprocal of a high cut-off frequency of a pass band of an ultrasound system for forming the contrast-enhanced ultrasound image.

In the method of generating an ultrasound signal according to the embodiment of the present disclosure, a pulse width of the damping compensation pulse has a value of 3.125 ns to 50 ns.

In the method of generating an ultrasound signal according to the embodiment of the present disclosure, the pair of pulses and the damping compensation pulse are generated to have an identical voltage.

In the method of generating an ultrasound signal according to the embodiment of the present disclosure, the voltage of the pulses is in a range of 1 to 5V.

In the method of generating an ultrasound signal according to the embodiment of the present disclosure, the damping compensation pulse attenuates an undamped component generated by the pair of pulses to improve the quality of the contrast-enhanced ultrasound image.

In the method of generating an ultrasound signal according to the embodiment of the present disclosure, damping compensation pulses included in a non-inverting and inverting output pulses for forming a contrast-enhanced ultrasound image, and generating a pulse width of the damping compensation pulses included in the non-inverting and inverting output pulses to have the same pulse width, or to have a different pulse width.

According to another embodiment, an ultrasound system includes a processing unit configured to generate a pair of pulse control signals (n, n+1) and a damping compensation pulse control signal, to generate a pair of pulses (n, n+1) having polarities opposite to each other and a damping compensation pulse having a polarity opposite to that of the n+1-th pulse based on the pair of pulse control signals and the damping compensation pulse control signal, to transmit transmission signals including the pair of pulses and the damping compensation pulse; and to successively generate the damping compensation pulse after generating the pair of pulses; and an ultrasound probe configured to generate an ultrasound signal based on the transmission signals, to transmit the ultrasound signal to a target object, and to acquire echo signals for forming a contrast-enhanced ultrasound image of the target object.

In the ultrasound system according to the embodiment of the present disclosure, a pulse width of the damping compensation pulse has a value lower than a reciprocal of a high cut-off frequency of a pass band of the ultrasound system for forming the contrast-enhanced ultrasound image.

In the ultrasound system according to the embodiment of the present disclosure, a pulse width of the damping compensation pulse has a value of 3.125 ns to 50 ns.

In the ultrasound system according to the embodiment of the present disclosure, the processing unit generates the pair of pulses and the damping compensation pulse to have an identical voltage.

In the ultrasound system according to the embodiment of the present disclosure, the voltage of the pulses is in a range of 1 to 5V.

In the ultrasound system according to the embodiment of the present disclosure, the processing unit causes the damping compensation pulse to attenuate an undamped component generated by the pair of pulses to improve the quality of the contrast-enhanced ultrasound image.

In the ultrasound system according to the embodiment of the present disclosure, the processing unit generates damping compensation pulses to include in each of a non-inverting and inverting output pulses for forming a contrast-enhanced ultrasound image, and generates a pulse width of the damping compensation pulses included in the non-inverting and inverting output pulses to have same pulse width, or to have different pulse width.

According to the present disclosure, the quality of a contrast-enhanced ultrasound image can be improved by reducing undamped components that may be generated upon the formation of a contrast-enhanced ultrasound image.

BRIEF DESCRIPTION OF THE DRAWINGS

FIG. 7 is a flowchart showing a procedure of generating an ultrasound signal according to an embodiment of the present disclosure.

DETAILED DESCRIPTION

Figure 1:
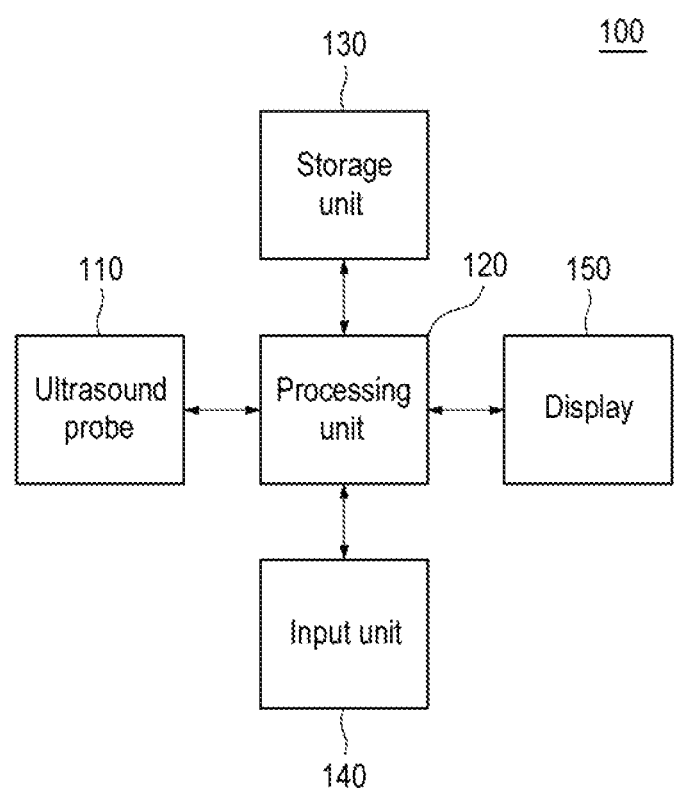
FIG. 1 is a block diagram schematically showing a configuration of an ultrasound system according to an embodiment of the present disclosure.

Embodiments of the present disclosure are illustrated for describing the technical spirit of the present disclosure. The scope of the claims according to the present disclosure is not limited to the embodiments described below or to detailed descriptions of these embodiments.

All technical or scientific terms used herein have meanings that are generally understood by a person having ordinary knowledge in the art to which the present disclosure pertains, unless otherwise specified. The terms used herein are selected for only more clear illustration of the present disclosure, and are not intended to limit the scope of claims in accordance with the present disclosure.

The expressions "include", "provided with", "have" and the like used herein should be understood as open-ended terms connoting the possibility of inclusion of other embodiments, unless otherwise mentioned in a phrase or sentence including the expressions.

A singular expression can include meanings of plurality, unless otherwise mentioned, and the same is applied to a singular expression stated in the claims.

The term "unit" used in these embodiments means a software component or hardware component, such as a field-programmable gate array (FPGA) and an application specific integrated circuit (ASIC). However, a "unit" is not limited to software and hardware, it may be configured to be an addressable storage medium or may be configured to run on one or more processors. For example, a "unit" may include components, such as software components, object-oriented software components, class components, and task components, as well as processors, functions, attributes, procedures, subroutines, segments of program codes, drivers, firmware, micro-codes, circuits, data, databases, data structures, tables, arrays, and variables. Functions provided in components and "unit" may be combined into a smaller number of components and "units" or further subdivided into additional components and "units."

The expression "based on" used herein is used to describe one or more factors that influences a decision, an action of judgment or an operation described in a phrase or sentence including the relevant expression, and this expression does not exclude additional factors influencing the decision, the action of judgment or the operation.

When a certain component is described as "coupled to" or "connected to" another component, this should be understood as having meaning that the certain component may be coupled or connected directly to the other component or that the certain component may be coupled or connected to the other component via a new intervening component.

Hereinafter, embodiments of the present disclosure will be described with reference to the accompanying drawings. In the accompanying drawings, like or relevant components are indicated by like reference numerals. In the following description of embodiments, repeated descriptions of the identical or relevant components will be omitted. However, even if a description of a component is omitted, such a component is not intended to be excluded in an embodiment.

The term "target object" used herein may be an object or a subject of which an ultrasound image is obtained using an ultrasound system, and may be a biological object or inanimate object. In addition, if the target object is a biological object, the target object may mean a part of a human body, and a fetus or an organ such as liver, heart, uterus, brain, breast, abdomen, blood vessel (or blood flow) may be included in the target object, and any one section through the human body may be included in the target object. In addition, a "user" mentioned herein indicates medical professionals capable of operating and using the ultrasound system, and may be doctors, nurses, medical technologists, sonographers or other medical image experts, but is not limited thereto.

FIG. 1 is a block diagram schematically showing a configuration of an ultrasound system according to an embodiment of the present disclosure.

As shown in FIG. 1, the ultrasound system 100 may include an ultrasound probe 110, a processing unit 120, a storage unit 130, an input unit 140 and a display 150. The ultrasound probe 110 is a sensor used to obtain clinical information such as spatial information, anatomy and the like of a target object by transmitting an ultrasound signal to the target object, receiving an ultrasound signal (or echo signal) reflected from the target object, and providing the received ultrasound signal to the ultrasound system 100. In this disclosure, the term "ultrasound probe" may be used as the same meaning as an ultrasound transducer or the like and may include, for example, a convex probe, a linear probe and the like. However, the ultrasound probe may not be limited thereto. The ultrasound probe 110 may include a plurality of piezoelectric elements (not shown) that transforms an electrical signal into an ultrasound signal and vice versa, and may transmit the ultrasound signal to the target object in response to the electrical signal (hereinafter, referred to as a "transmission signal") input into the plurality of piezoelectric elements. The target object may be a body (e.g., a part or an organ of a body of a human being, including a blood vessel, a heart, a liver or the like) into which a contrast agent is injected, and the body may include normal tissues or lesions (e.g., a cancer tissue, coagulated blood and the like). The contrast agent injected into the body includes particulates containing a gas such as micro-bubbles and moves along the blood vessels. The particulates included in the contrast agent are subjected to an external pressure (e.g., ultrasound signals) and repeat relaxation and contraction, and explode when they are subjected to a pressure higher than a threshold value. When the particulates explode, an echo signal having the strength higher than those of normal tissues around the particulates may be generated. Accordingly, since an area including the contrast agent in an ultrasound image may be displayed to be relatively brighter than the other areas that do not contain the contrast agent, an enhanced effect may be obtained in a specific area of the target body. Further, when the ultrasound probe 110 acquires an echo signal reflected from the target object that has received the ultrasound signal, the ultrasound probe 110 may convert the acquired echo signal into an electrical signal (hereinafter, referred to as a "reception signal"). In one embodiment, the ultrasound probe 110 may output a plurality of ultrasound signals in response to a plurality of transmission signals transmitted from the processing unit 120. Further, the ultrasound probe 110 may receive a plurality of echo signals reflected from the target object in response to the plurality of ultrasound signals transmitted to the target object and generate a plurality of reception signals.

In order to generate ultrasound signals of the ultrasound probe 110 used in a contrast-enhanced ultrasound image mode for forming a contrast-enhanced ultrasound image, the processing unit 120 may generate a pair of pulse control signals n and n+1 and a damping compensation pulse control signal. Further, the processing unit 120 may generate a pair of pulses n and n+1 having polarities opposite to each other and a damping compensation pulse having a polarity opposite to that of the n+1-th pulse, based on the pair of pulse control signals and the damping compensation pulse control signal. In one embodiment, if the n-th pulse has + polarity and the n+1-th pulse has − polarity, the damping compensation pulse may have + polarity; and if the n-th pulse has − polarity and the n+1-th pulse has + polarity, the damping compensation pulse may have − polarity. Further, the processing unit 120 generates a non-inverting output pulse and an inverting output pulse. Here, the non-inverting output pulse and the inverting output pulse have polarities opposite to each other to remove linear components and to represent non-linear components in the contrast-enhanced ultrasound image, and each of the non-inverting and inverting output pulses include the damping compensation pulses. That is, the processing unit 120 may generate a non-inverting output pulse control signal including the pair of the pulse control signals and the damping compensation pulse control signal, and an inverting output pulse control signal including the pair of the pulse control signals and the damping compensation pulse control signal. The processing unit 120 may generate the pulse width of the damping compensation pulses included in the non-inverting and inverting output pulses to have same pulse width, or generate the pulse width slightly different from each other. It is possible to enhance the pulse cancellation by generating the pulse width of the damping compensation pulses included in the non-inverting and inverting output pulses to have slightly different pulse width. Further, the processing unit 120 may generate the non-inverting output pulse and the inverting output pulse having the polarity opposite to that of the non-inverting output pulse based on the non-inverting output pulse control signal and the inverting output pulse control signal. In one embodiment, if the n-th pulse of the non-inverting output pulse has − polarity, the n+1-th pulse has + polarity, and the damping compensation pulse has − polarity; the n-th pulse of the inverting output pulse may have + polarity, the n+1-th pulse may have − polarity, and the damping compensation pulse may have + polarity. In another embodiment, if the n-th pulse of the non-inverting output pulse has + polarity, the n+1-th pulse has − polarity, and the damping compensation pulse has + polarity; the n-th pulse of the inverting output pulse may have − polarity, the n+1-th pulse may have + polarity, and the damping compensation pulse may have − polarity.

Further, the processing unit 120 forms a contrast-enhanced ultrasound image of the target object based on a plurality of reception signals received from the ultrasound probe 110. In one embodiment, the processing unit 120 may generate ultrasound data corresponding to the contrast-enhanced ultrasound image by performing various signal processing (e.g., low pass filtering, gain adjustment, scan converting, etc.) on the plurality of reception signals received from the ultrasound probe 110. In one embodiment, the ultrasound data includes RF (radio frequency) data or IQ (in-phase/quadrature) data. However, the ultrasound data may not be limited thereto. Further, the processing unit 120 may generate the damping compensation pulse subsequent to the generation of the pair of pulses. The shapes of the pair of pulses and the damping compensation pulse generated by the processing unit 120 will be described below.

The storage unit 130 may store the contrast-enhanced ultrasound image of the target object formed by the processing unit 120. In one embodiment, the storage unit 130 may include a hard disk, non-volatile memory, CD-ROM (Compact Disc-Read Only Memory), DVD-ROM (Digital Versatile Disc-Read Only Memory) and the like. However, the storage unit may not be limited thereto.

The input unit 140 may receive input information from a user. The input information may include a selection of ultrasound image modes for forming an ultrasound image in the ultrasound system 100 by the user. In one embodiment, the ultrasound image modes may include a B mode capable of representing the target object as an ultrasound image of a two-dimensional shape, a Doppler mode capable of representing a moving target object as consecutive ultrasound images using a Doppler effect, the contrast-enhanced ultrasound image mode capable of forming the contrast-enhanced ultrasound image of the target object, etc. However, the ultrasound image mode may not be limited thereto. In one embodiment, the input unit 140 may include a control panel, a trackball, a keyboard, a mouse, a touch screen, etc. However, the input unit may not be limited thereto.

The display 150 may display the contrast-enhanced ultrasound image of the target object formed by the processing unit 120. In one embodiment, the display 150 may include a liquid crystal display (LCD), a light emitting diode (LED) display, an organic light-emitting diode (OLED) display or the like. However, the display may not be limited thereto.

Figure 2:
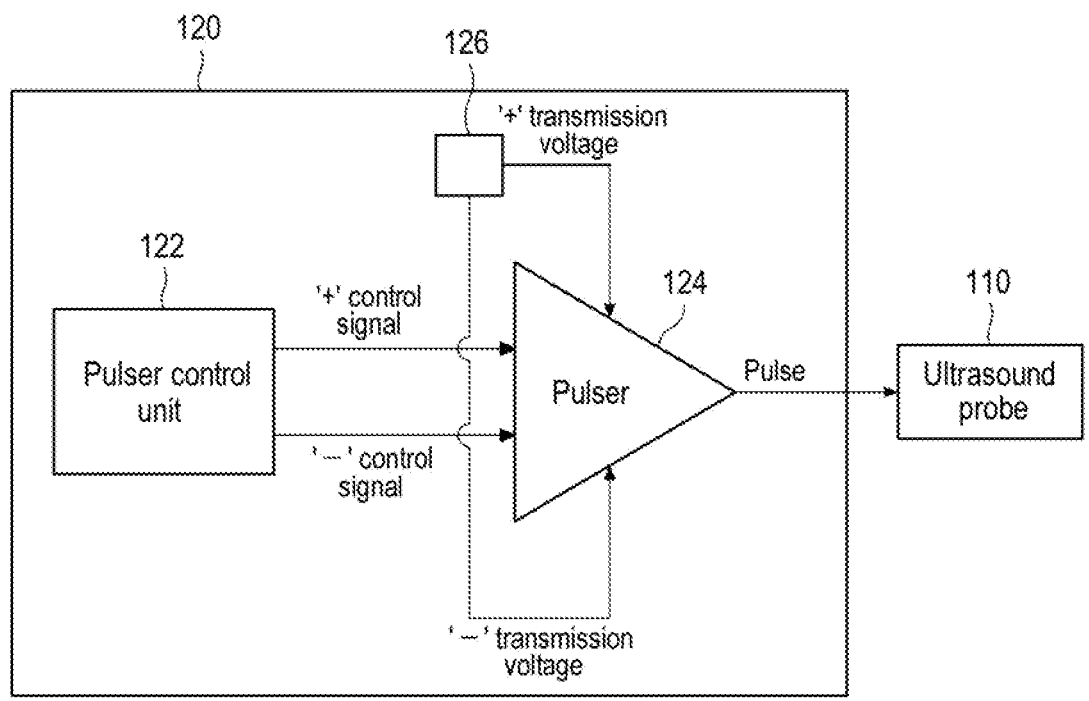
FIG. 2 is a block diagram schematically showing a configuration of a processing unit according to an embodiment of the present disclosure.

FIG. 2 is a block diagram schematically showing a configuration of a processing unit 120 according to an embodiment of the present disclosure.

As shown in FIG. 2, the processing unit 120 includes a pulser control unit 122, a pulser 124 and a voltage generator 126.

In order to form a contrast-enhanced ultrasound image of a target object, the pulser control unit 122 may generate a pulse control signal for controlling pulses generated by the pulser 124. In one embodiment, the pulse control signal may include a pair of pulse control signals n and n+1 and a damping compensation pulse control signal. The pulse control signal may include a + control signal for generating a pulse having + polarity and a − control signal for generating a pulse having − polarity. In one embodiment, the pulser control unit 122 may separately generate a + control signal and a − control signal so that the + control signal and the − control signal may be input into different ports of the pulser 124. Further, the pulser control unit 122 may generate the pulse control signal so that the pair of pulses n and n+1 for forming the contrast-enhanced ultrasound image may have polarities different from each other. That is, the pulser control unit 122 may generate the + control signal so that the n-th pulse of the pair of pulses may have + polarity, generate the − control signal so that the n+1-th pulse may have − polarity, generate the − control signal so that the n-th pulse may have − polarity, and generate the + control signal so that the n+1-th pulse may have + polarity. Further, the pulser control unit 122 may generate the pulse control signal so that the n+1-th pulse and the damping compensation pulse may have polarities different from each other. That is, the pulser control unit 122 may generate the − control signal so that the n+1-th pulse may have − polarity, generate the + control signal so that the damping compensation pulse may have + polarity, generate the + control signal so that the n+1-th pulse may have + polarity, and generate the − control signal so that the damping compensation pulse may have − polarity, The pulser 124 may generate a pulse based on the pulse control signal received from the pulser control unit 122. Further, the pulser 124 may receive a transmission voltage according to an input ultrasound image mode, from the voltage generator 126 so as to generate a pulse having a predetermined voltage. In one embodiment, the pulser 124 may receive a low voltage of 1 to 5V as a transmission voltage in the contrast-enhanced ultrasound image mode for forming a contrast-enhanced ultrasound image. Further, the pulser 124 may generate a pulse having + polarity and corresponding to the magnitude of the transmission voltage when the pulser 124 receives a + control signal from the pulser control unit 122, and may generate a pulse having − polarity and corresponding to the magnitude of the transmission voltage when the pulser 124 receives a − control signal from the pulser control unit 122. In one embodiment, when 5V is received as a transmission voltage, the pulser 124 may generate a pulse of +5V if the pulser 124 receives a + control signal and may generate a pulse of −5V if the pulser 124 receives a − control signal. Further, the pulser 124 may generate a pair of pulses n and n+1 and a damping compensation pulse to have the same voltage. In one embodiment, voltages of the pair of pulses n and n+1 and the damping compensation pulse may be set to have a range of 1 to 5V in the contrast-enhanced ultrasound image mode. However, the voltage may not be limited thereto.

The voltage generator 126 may generate a constant voltage using a Zener diode or the like, which is a kind of semiconductor diode having a PN junction structure.

Figure 3:
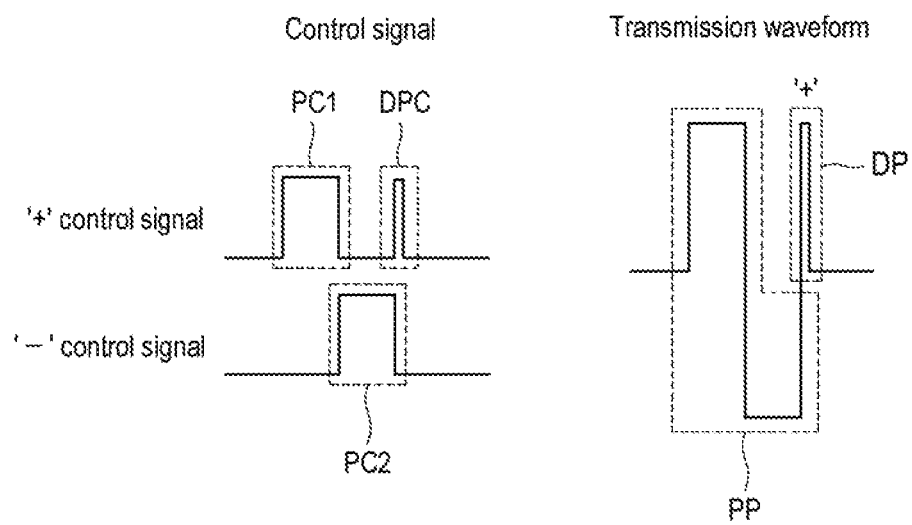
FIG. 3 is an illustrative view schematically showing pulse control signals and pulse generates according to an embodiment of the present disclosure.

FIG. 3 is an illustrative view schematically showing pulse control signals and pulse generates according to an embodiment of the present disclosure.

As shown in FIG. 3, the pulser control unit 122 may separately generate a + control signal and a − control signal. In one embodiment, in case of the n-th pulse control signal PC1 is a + control signal, the n+1-th pulse control signal PC2 is a − control signal, and the damping compensation pulse control signal DPC is a + control signal, the damping compensation pulse control signal DPC may be generated together with the n-th pulse control signal PC1 to be input into an identical port of the pulser 124, and the n+1-th pulse control signal PC2 may be separately generated to be input into the pulser 124 through a port different from that of the n-th pulse control signal PC1 and the damping compensation pulse control signal DPC. If the pulser 124 receives the control signals PC1, PC2 and DPC shown in the figure from the pulser control unit 122, the pulser 124 may generate a transmission waveform shown in the figure, i.e., a pulse in which a pair of pulses PP and a damping compensation pulse DP are successively generated.

Figure 4:
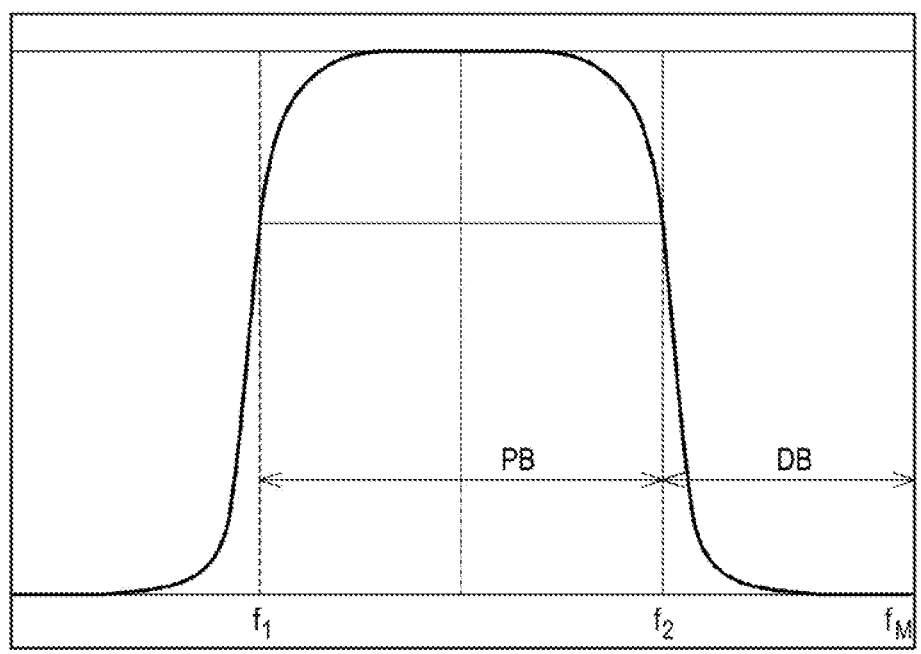
FIG. 4 is an illustrative view schematically showing a relationship between a frequency of a damping compensation pulse and a pass band in the ultrasound system according to the embodiment of the present disclosure.

FIG. 4 is an illustrative view schematically showing a relationship between a frequency of a damping compensation pulse and a pass band in the ultrasound system according to the embodiment of the present disclosure.

As shown in FIG. 4, the pulser control unit 122 may generate a damping compensation pulse control signal such that a damping compensation pulse may have a predetermined pulse width that concentrates its energy outside the pass band PB and within the dead band DB, and the pulse width that concentrates its energy outside the pass band PB and within the dead band DB of the damping compensation pulse may have a value lower than the reciprocal of a high cut-off frequency $f_2$ of the pass band PB of the ultrasound system 100 for forming a contrast-enhanced ultrasound image and a value higher than the reciprocal of the frequency $f_M$ of a master clock received from the pulser control unit 122 to generate a pulse control signal. In one embodiment, a low cut-off frequency $f_1$ of the ultrasound system 100 may have a value of 1 MHz, and the high cut-off frequency $f_2$ may have a value of about 20 MHz. However, the low cut-off frequency $f_1$ and the high cut-off frequency $f_2$ may not be limited thereto. In one embodiment, the frequency $f_M$ of the master clock of the ultrasound system 100 may have a value of about 40 to 320 MHz, and the pulse width that concentrates its energy outside the pass band PB and within the dead band DB of the damping compensation pulse may be set to have a value of about 3.125 ns to 50 ns. However, the pulse width that concentrates its energy outside the pass band PB and within the dead band DB of the damping compensation pulse may not be limited thereto.

Figure 5A:
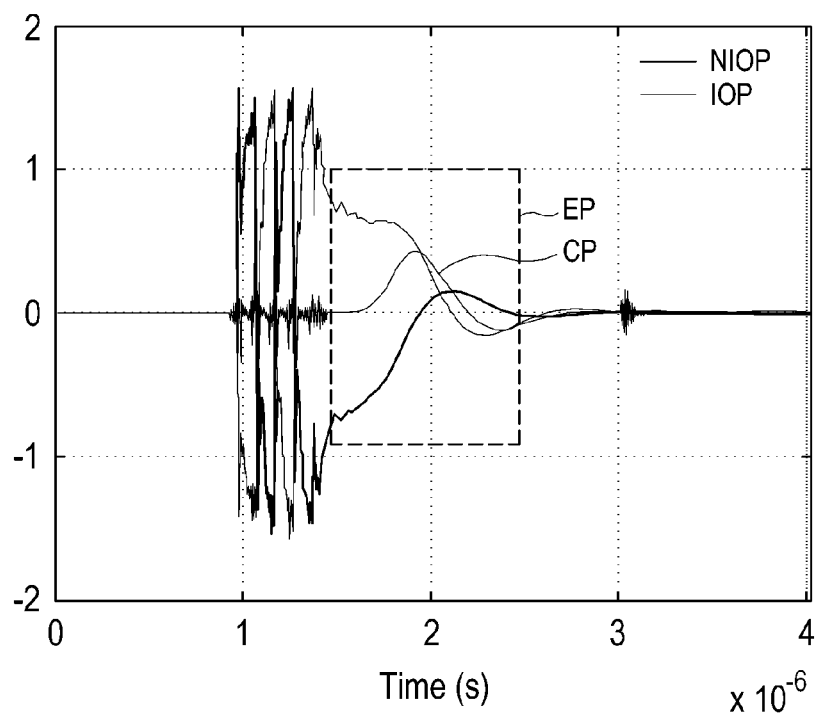
FIGS. 5A and 5B are illustrative views showing an attenuated effect of an undamped component at the output pulse in a time domain.
Figure 5B:
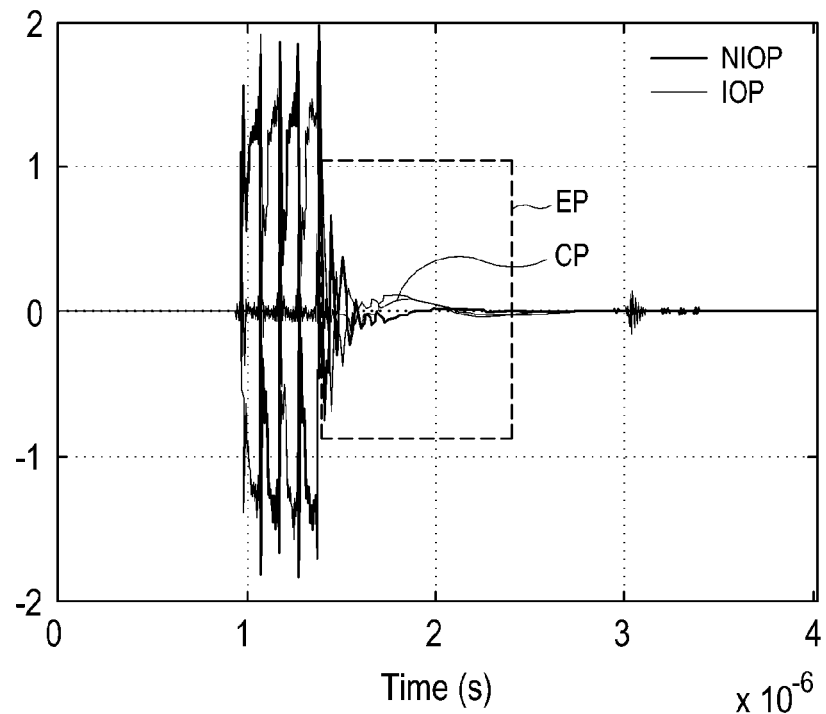

FIGS. 5A and 5B are illustrative views showing an attenuated effect of an undamped component at the output pulse in a time domain.

As shown in FIG. 5A, if each of the non-inverting output pulse ("NIOP") and the inverting output pulse ("IOP") does not include the damping compensation pulse, the NIOP, the TOP, and a composite pulse ("CP") of the NIOP and IOP may not be sufficiently attenuated at an end portion ("EP") due to a capacitive loading effect. On the other hand, if each of the NIOP and the IOP's includes the damping compensation pulse having the polarity opposite to that of the last pulse of the NIOP and the IOP, respectively, as shown in FIG. 5B, the undamped component for each of the NIOP, the IOP, and a CP may remarkably be decreased towards the EP. The quality of the contrast-enhanced ultrasound image can be improved by reducing the undamped components that may be generated upon the formation of the contrast-enhanced ultrasound image.

Figure 6A:
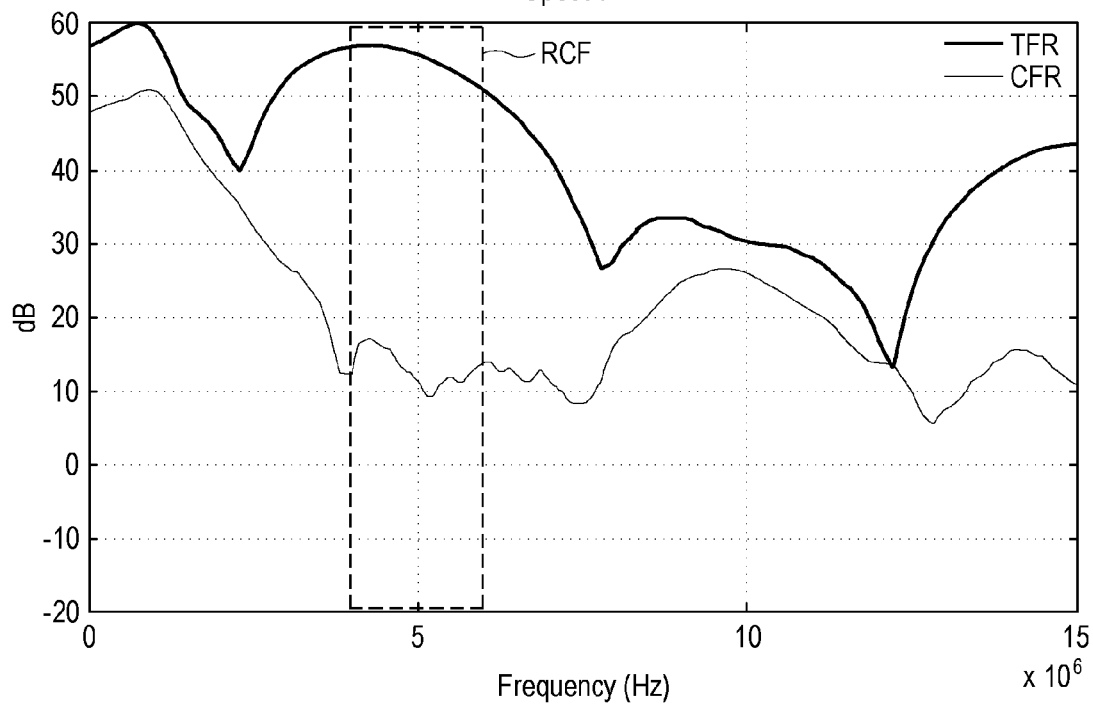
FIGS. 6A and 6B are illustrative views showing an attenuated effect of an undamped component at the output pulse in a frequency domain.
Figure 6B:
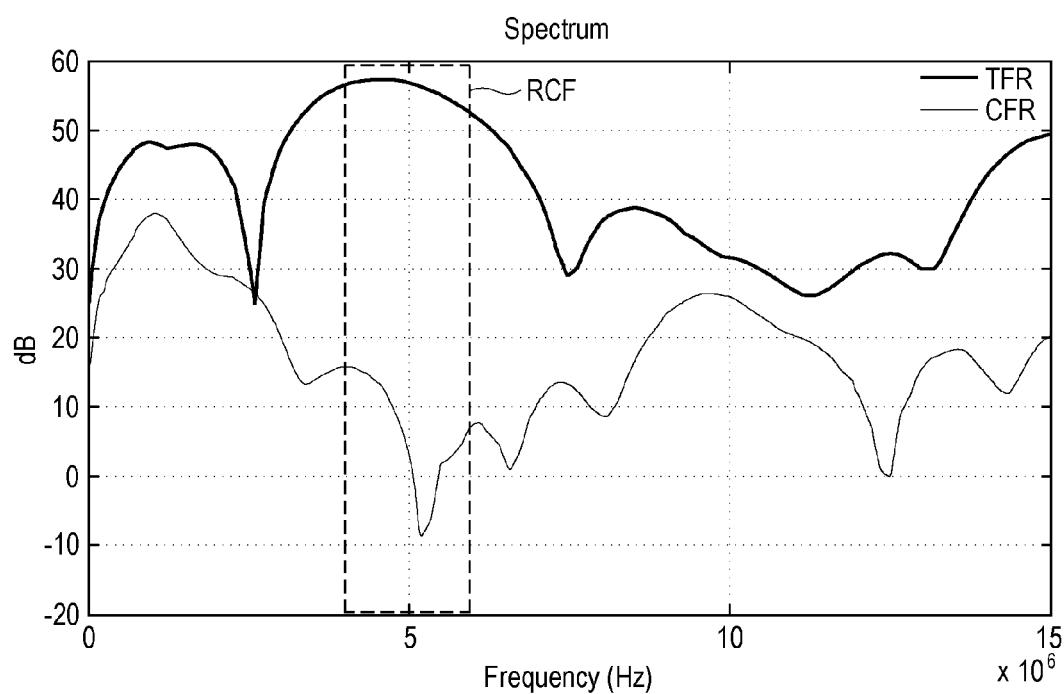

FIGS. 6A and 6B are illustrative views showing an attenuated effect of an undamped component at the output pulse in a frequency domain.

Difference between a frequency response TFR caused by the non-inverting output pulse or the inverting output pulse and a frequency response CFR caused by the composite pulse of the non-inverting and the inverting output pulse may be represented as a pulse cancellation performance, and the unit for the pulse cancellation performance may be represented as dB.

As shown in FIG. 6A, if each of the non-inverting and the inverting output pulse does not include the damping compensation pulse, the pulse cancellation performance at a region RCF in a center frequency (ex. 5 MHz) of the ultrasound system 100 is about 45 dB. On the other hand, as shown in FIG. 6B, if each of the non-inverting and the inverting output pulse includes the damping compensation pulse, the pulse cancellation performance at a region RCF in the center frequency of the ultrasound system 100 is about 65 dB. Therefore, the pulse cancellation performance is increased about 20 dB due to the damping compensation pulse.

FIG. 7 is a flowchart showing a procedure of generating an ultrasound signal according to an embodiment of the present disclosure.

Although process steps, method steps or algorithms are illustrated in a sequential order in the flowchart, such processes, methods, algorithms may be configured to be operated in any suitable order. In other words, certain sequences or orders of steps to be described in the present disclosure are not necessarily performed in the order described in the present disclosure. Further, even though some steps are explained as being performed non-simultaneously, these steps may be simultaneously performed in another embodiment. Moreover, the illustration of the processes depicted in the figure does not mean that the illustrated processes exclude other changes and modifications made thereto, that any of the illustrated processes or the steps thereof is essential for one or more of the present disclosure(s), and that the illustrated processes are desirable.

As shown in FIG. 7, at step S710, a pair of pulse control signals n and n+1 and a damping compensation pulse control signal are generated. For example, referring to FIGS. 1 to 4, the processing unit 120 of the ultrasound system 100 generates a pair of pulse control signals and a damping compensation pulse control signal to form a contrast-enhanced ultrasound image. Here, the pulse control signals may be generated so that a pair of pulses and a damping compensation pulse may be successively generated. Therefore, the n-th pulse, the n+1-th pulse and the damping compensation pulse may be successively generated on a time basis, like the transmission waveform shown in FIG. 3.

Further, at step S720, a pair of pulses having polarities opposite to each other and a damping compensation pulse having a polarity opposite to that of the n+1-th pulse are generated. For example, referring to FIGS. 1 to 4, the processing unit 120 of the ultrasound system 100 may generate a pair of pulses n and n+1 having polarities opposite to each other and a damping compensation pulse having a polarity opposite to that of the n+1-th pulse, using the pair of pulse control signals and the damping compensation pulse control signal. Here, the damping compensation pulse may be successively generated after the generation of the pair of pulses.

Further, at step S730, transmission signals including the pair of pulses and the damping compensation pulse are transmitted to an ultrasound probe. For example, referring to FIGS. 1 to 4, the processing unit 120 of the ultrasound system 100 may generate transmission signals including a pair of pulses and a damping compensation pulse and transmit the transmission signals to the ultrasound probe 110.

Further, at step S740, echo signals for forming a contrast-enhanced ultrasound image may be acquired. For example, referring to FIGS. 1 to 4, the ultrasound probe 110 may generate ultrasound signals based on the transmission signals received from the processing unit 120 and acquire echo signals of the ultrasound signals reflected from the target object. The ultrasound probe 110 may generate a plurality of reception signals using the echo signals, and the processing unit 120 may form a contrast-enhanced ultrasound image of the target object using the plurality of the reception signals.

While the foregoing methods have been described with respect to particular embodiments, these methods may also be implemented as computer-readable codes on a computer-readable recording medium. The computer-readable recoding medium includes any kind of data storage devices that can be read by a computer system. Examples of the computer-readable recording medium includes ROM, RAM, CD-ROM, magnetic tape, floppy disk, optical data storage device and the like, and also include that implemented in the form of a carrier wave (e.g., transmission via Internet). Also, the computer-readable recoding medium can be distributed to the computer systems which are connected through a network so that the computer-readable codes can be stored and executed in a distribution manner. Further, the functional programs, codes and code segments for implementing the foregoing embodiments can easily be inferred by programmers in the art to which the present disclosure pertains.

Although the specific embodiments have been described above, these embodiments are presented by way of examples and should not be interpreted as limiting the scope of the disclosure. The novel methods and devices of this specification may be implemented in various other forms, and various omissions, substitutions and changes may also be made to the embodiments disclosed herein without departing from the spirit of the disclosure. The claims appended to the specification and equivalents thereof should be interpreted to include all the forms and modifications included in the scope and spirit of the disclosure.

What is claimed is:

1. A method of generating an ultrasound signal of an ultrasound probe used in a contrast-enhanced ultrasound image mode, the method comprising:

generating a pair of pulse control signals (n, n+1) and a damping compensation pulse control signal;

generating a pair of pulses (n, n+1) having polarities opposite to each other and a damping compensation pulse having a polarity opposite to that of the pulse (n+1) based on the pair of pulse control signals (n, n+1) and the damping compensation pulse control signal;

transmitting transmission signals including the pair of pulses (n, n+1) and the damping compensation pulse to the ultrasound probe, the transmission signals forming a single transmission waveform of the pair of pulses (n, n+1) and the damping compensation pulse as successively connected together, wherein the single transmission waveform is a continuous bi-polar waveform with the pair of pulses having equal width and the damping compensation pulse at an end of the continuous bi-polar waveform having a narrower width than the equal width; and generating an ultrasound signal in the ultrasound probe based on the transmission signals, transmitting the ultrasound signal to a target object, and acquiring echo signals for forming a contrast-enhanced ultrasound image of the target object from the target object, wherein the damping compensation pulse is successively generated after successively generating the pair of pulses (n, n+1).

2. The method of claim 1, wherein a pulse width of the damping compensation pulse has a value lower than a reciprocal of a high cut-off frequency of a pass band of an ultrasound system for forming the contrast-enhanced ultrasound image.

3. The method of claim 1, wherein a pulse width of the damping compensation pulse has a value of 3.125 ns to 50 ns.

4. The method of claim 1, wherein the pair of pulses (n, n+1) and the damping compensation pulse are generated to have an identical voltage.

5. The method of claim 4, wherein the voltage of the pulses is in a range of 1 to 5V.

6. The method of claim 1, wherein the damping compensation pulse attenuates an undamped component generated by the pair of pulses (n, n+1) to improve a quality of the contrast-enhanced ultrasound image.

7. The method of claim 1, wherein damping compensation pulses are included in a non-inverting output pulse and an inverting output pulse for forming a contrast-enhanced ultrasound image, and generating a pulse width of the damping compensation pulses included in the non-inverting and inverting output pulses to have same pulse width, or to have different pulse width.

8. The method of claim 1 wherein transmitting comprises transmitting the single transmission waveform as only the pair of pulses and the damping compensation pulse as the continuous bi-polar waveform, the continuous bi-polar waveform beginning and ending at a middle voltage with only crossings of the middle voltage within the continuous bi-polar waveform.

9. The method of claim 1 wherein the continuous bi-polar waveform begins and ends at a middle voltage with only crossings of the middle voltage within the continuous bi-polar waveform.

10. An ultrasound system comprising:

a processing unit configured to generate a pair of pulse control signals (n, n+1) and a damping compensation pulse control signal, to generate a pair of pulses (n, n+1) having polarities opposite to each other and a damping compensation pulse having a polarity opposite to that of the pulse (n+1) based on the pair of pulse control signals (n, n+1) and the damping compensation pulse control signal, to transmit transmission signals including the pair of pulses (n, n+1) and the damping compensation pulse; and to successively generate the damping compensation pulse after generating the pair of pulses (n, n+1) as part of a same continuous waveform of the pair of pulses and the damping compensation pulse with the damping compensation pulse having a pulse width less than a pulse width of the immediately preceding pulse n+1 of the pair of pulses (n, n+1); and an ultrasound probe configured to generate an ultrasound signal based on the transmission signals, to transmit the ultrasound signal to a target object, and to acquire echo signals for forming a contrast-enhanced ultrasound image of the target object from the target object.

11. The system of claim 10, wherein the pulse width of the damping compensation pulse has a value lower than a reciprocal of a high cut-off frequency of a pass band of the ultrasound system for forming the contrast-enhanced ultrasound image.

12. The system of claim 10, wherein the pulse width of the damping compensation pulse has a value of 3.125 ns to 50 ns.

13. The system of claim 10, wherein the processing unit generates the pair of pulses (n, n+1) and the damping compensation pulse to have an identical voltage.

14. The system of claim 13, wherein the voltage of the pulses is in a range of 1 to 5V.

15. The system of claim 10, wherein the processing unit causes the damping compensation pulse to attenuate an undamped component generated by the pair of pulses (n, n+1) to improve a quality of the contrast-enhanced ultrasound image.

16. The system of claim 10, wherein the processing unit generates damping compensation pulses to include in each of a non-inverting output pulse and an inverting output pulse for forming a contrast-enhanced ultrasound image, and generates a pulse width of the damping compensation pulses included in the non-inverting and inverting output pulses to have same pulse width, or to have different pulse width.

* * * * *